United States Patent [19]
Lin

[11] Patent Number: 5,507,746
[45] Date of Patent: Apr. 16, 1996

[54] HOLDING AND FIXING MECHANISM FOR ORTHOPEDIC SURGERY

[76] Inventor: Chih-I Lin, 14292 Spring Vista La., Chino Hills, Calif. 91709

[21] Appl. No.: 280,659

[22] Filed: Jul. 27, 1994

[51] Int. Cl.⁶ .......................... A61B 17/70; A61B 17/86; A61B 17/68
[52] U.S. Cl. ................. 606/61; 606/73; 606/60; 403/400
[58] Field of Search .................. 606/61, 60, 73; 403/400, 395

[56] References Cited

U.S. PATENT DOCUMENTS

| | | | |
|---|---|---|---|
| 581,195 | 4/1897 | Chardlee | 403/395 |
| 5,196,014 | 3/1993 | Lin | 606/61 |
| 5,224,954 | 6/1993 | Baker et al. | 606/61 |
| 5,281,222 | 1/1994 | Allard et al. | 606/61 |

FOREIGN PATENT DOCUMENTS 9311715  6/1993  WIPO ...................................... 606/61

*Primary Examiner*—Stephen C. Pellegrino
*Assistant Examiner*—Scott B. Markow
*Attorney, Agent, or Firm*—Bacon & Thomas

[57] ABSTRACT

A holding and fixing mechanism for an orthopedic surgery makes use of a holding plug to fasten together a U-shaped clamping block, a wedging element and a rod body. The clamping block is provided with two through holes capable of cooperating with a wedging portion of the wedging element and the holding plug so as to form an appropriate angle as required between the wedging element and the U-shaped clamping block. The fixation position of the wedging element can be easily adjusted. The holding and fixing mechanism is attained by the knurl-fastening method in place of the conventional screw-fastening method.

17 Claims, 4 Drawing Sheets

HOLDING AND FIXING MECHANISM FOR ORTHOPEDIC SURGERY

FIELD OF THE INVENTION

The present invention relates generally to an orthopedic device, and more particularly to a holding and fixing mechanism for orthopedic surgery.

BACKGROUND OF THE INVENTION

The conventional fixing mechanism for fastening to a vertebral fixation rod is generally provided with a screw, which is used to fasten a vertebra intended to be fixed and which is also used to urge forcibly the vertebra to remain on the vertebral fixation rod and the like, as exemplified by the U.S. Pat. Nos. 5,261,913; 4,887,596; and 5,257,993. Such fastening methods as described above are defective in design in that a slight intervertebral motion can often cause the fastening screw of the fixing mechanism to become loosened or even detached.

SUMMARY OF THE INVENTION

It is therefore the primary objective of the present invention to provide a wedging form of holding and fixing mechanism for use in the surgical treatment of a fractured bone.

It is another objective of the present invention to provide a holding and fixing mechanism capable of causing forcibly a vertebral fixation rod and a bone screw, which is located by a side of the vertebral fixation rod, to diverge perpendicularly so as to form therebetween a specific angle.

It is still another objective of the present invention to provide an orthopedic holding and fixing mechanism which is composed of a U-shaped clamping block, a wedging element, a holding plug, and a rod.

In keeping with the principle of the present invention, the foregoing objectives of the present invention are accomplished by a holding and fixing mechanism for surgical treatment of a fractured bone, which is made up of the component parts described explicitly hereinafter.

A U-shaped clamping block of a substantially curve U-shaped construction is composed of a left plate and a right plate, which are provided respectively and correspondingly with a through hole.

A wedging element has one end provided with a fastening means for fastening the wedging element onto a vertebra or/and other vertebral fixation device. The wedging element has another end serving as a wedging portion having parallel grooves or knurls.

A rod body is disposed between the U-shaped clamping block and the wedging element.

A holding plug is lodged securely between the U-shaped curve portion of the U-shaped clamping block and the rod body. The holding plug may be also lodged securely between the wedging portion of the wedging element and the rod body. The holding plug is provided in one side thereof with holding grooves, which form a columnar holding hole in conjunction with the U-shaped curve portion of the U-shaped clamping block or with the parallel grooves of the wedging portion of the wedging element. In other words, the holding plug is capable of holding securely the rod body by means of the columnar holding hole.

The holding and fixing mechanism of the present invention is characterized in that a specific angle is formed by the left and the right plates of the U-shaped clamping block and the line connecting the axes of the two through holes of the left and the right plates of the U-shaped clamping block, thereby facilitating the wedging element and the left and the right plates of the U-shaped clamping block to form therebetween, in cooperating with the wedging portion of the wedging element and the holding plug, a specific angle ranging approximately between 75 degrees and 105 degrees.

The component parts of the holding and fixing mechanism of the present invention are made of any biocompatible metal material suitable for use in the surgical treatment of a fractured bone, such as the iron-based stainless steel 316LVM, the titanium-based Ti-6-4, or the cobalt-molybdenum-chromium alloy.

The U-shaped clamping block of the holding and fixing mechanism of the present invention is integrally made up of one curve portion and two flat plates which are provided respectively with a through hole. The construction of the U-shaped clamping block is such that the holding and fixing mechanism of the present invention is provided with an adequate structural strength. The profile of the U-shaped clamping block is preferably U-shaped. However, such a U-shaped profile of the clamping block is not absolutely called for. For instance, it is not absolutely required that the left and the right plates of the clamping block must be parallel to each other even though they are preferably parallel to each other. A straight line can be formed by connecting the two axes of the two through holes of the left and the right plates of the U-shaped clamping block. The afore-mentioned straight line will be referred to as an axial line hereinafter in the specification. The axial line and the vertical line of the two plates of the U-shaped clamping block form a specific angle, such as zero degree, five degrees, ten degrees, fifteen degrees, etc. These two through holes are preferably provided on the inner wall surface thereof with the wedging tenons or parallel knurls, which are engageable with the parallel grooves or knurls of the wedging element. For example, these two through holes are provided with knurls forming a knurled surface which is substantially perpendicular to the axial line. As a result, the knurled surface and the surfaces of the left and the right plates form a specific angle, such as zero degree, five degrees, ten degrees, fifteen degrees, etc.

The wedging element of the present invention may be a fastening element, such as a bone screw or a bone hook, which is fastened directly onto a vertebra. The wedging element of the present invention may be also a coupling element, such as a connection rod, a threaded rod, or a horizontal auxiliary fixation rod, which is generally a component part of the fixation device for fixing a vertebra. The wedging element is provided at least on one side thereof with parallel grooves or knurls; nevertheless the wedging element is preferably provided on both sides thereof with knurls. If the wedging element is provided on one side thereof with parallel grooves, such parallel grooves are intended to form a columnar holding hole in conjunction with the holding grooves of the holding plug for the purpose of holding securely the rod body of the holding and fixing mechanism of the present invention. If another side of the wedging element is also provided thereon with parallel grooves, such parallel grooves of the wedging element are engageable with the wedging tenons of the two through holes of the U-shaped clamping block. If the wedging element is provided with knurls, such knurls are intended to fix solidly in place with the knurls of the two through holes of the U-shaped clamping block.

The wedging element may be of any shape. However, if the wedging element takes the form of a bone screw or a bone hook, the wedging portion of wedging element is preferably round in shape. On the other hand, if the wedging element takes the form of an auxiliary fixation rod or a threaded rod, the wedging portion of the wedging element is preferably of a columnar construction having an arcuate section.

The holding plug of the present invention may be of any shape. In addition, the holding plug has a thickness, which is measured in terms of a distance between the left and the right plates of the U-shaped clamping block and is preferably and substantially equal to the distance between the two plates of the U-shaped clamping block. The holding plug has a length, which is measured along the direction of the holding groove and is preferably and substantially equal to a width of the curve portion of the U-shaped clamping block. The holding groove of the holding plug is composed of one or more holding recessed claws or of one arcuate surface which is preferable. The arcuate shape of the U-shaped clamping block is dependent on the shape of the rod body intended to be held and must be based on the principle that the arcuate surface and the curve portion of the U-shaped block or the parallel grooves of the wedging portion of the wedging element form together a hollow cavity capable of holding securely the rod body. If necessary, the side opposite to the holding groove may be provided with knurls capable of cooperating with the knurled portion of the wedging element. The press end of the holding plug has a width which is substantially relative to a width of another end of the holding plug. Preferably, the press end has a slightly smaller width and is of a bevel construction in view of the fact that a bevel press end can be pressed in easily, and that the knurled surface of the holding plug can fix solidly in place with the knurled portion of the wedging element when the bevel press end is so pressed as to remain at a specific depth, and further that the holding plug is forced to move toward the curve portion of the U-shaped clamping block so as to retain securely the vertebral fixation rod. Furthermore, the press end of the holding plug may be provided, if necessary, with a retaining element, such as an elastic inverted retainer which can be forced to move inwards in a retrievable manner by an external force exerting thereon. In other words, as the holding plug is pressed in, the elastic inverted retainer is subsequently caused to withdraw. However, when the pressed holding plug is located, the elastic inverted retainer is allowed to bounce back up to be caught by another side of the press end of the U-shaped clamping block. If necessary, another side of the press end of the holding plug may be provided with the retaining element, which is preferably located on the side on which the holding groove is located.

it must be noted here that the rod-shaped main body of a holding object of the holding and fixing mechanism of the present invention is referred to as the rod body as described above. The rod body may be therefore a vertebral fixation rod, a threaded rod, an auxiliary fixation rod, the handle portion of a bone screw, or the handle portion of a bone hook.

The foregoing objectives, features and functions of the present invention will be more readily understood upon a thoughtful deliberation of the following detailed description of the embodiments of the present invention in conjunction with the accompanying drawings.

BRIEF DESCRIPTION OF THE DRAWINGS

FIG. 2-B is a side elevational view taken along line IIB—IIB in FIG. 2-A.

FIG. 2-C is a front elevational view of the U-shaped clamping block shown in FIG. 2-A.

FIG. 2-D is a schematic view of a section of the U-shaped clamping block of

FIG. 2-A in accordance with a first embodiment.

FIG. 2-E is a schematic view of a section of the U-shaped clamping block of FIG. 2-A in accordance with a second embodiment.

FIG. 2-F is a schematic view of section of the U-shaped clamping block of FIG. 2-A in accordance with a third embodiment.

FIG. 3-B is a front elevational view of the holding plug of FIG. 3-A.

FIG. 3-C is a right elevational view of the holding plug of FIG. 3-A.

FIG. 3-D is a rear elevational view of the holding plug if FIG. 3-A.

FIG. 3-E is a left elevational view of the holding plug of FIG. 3-A.

DETAILED DESCRIPTION OF THE INVENTION

Figure 1:
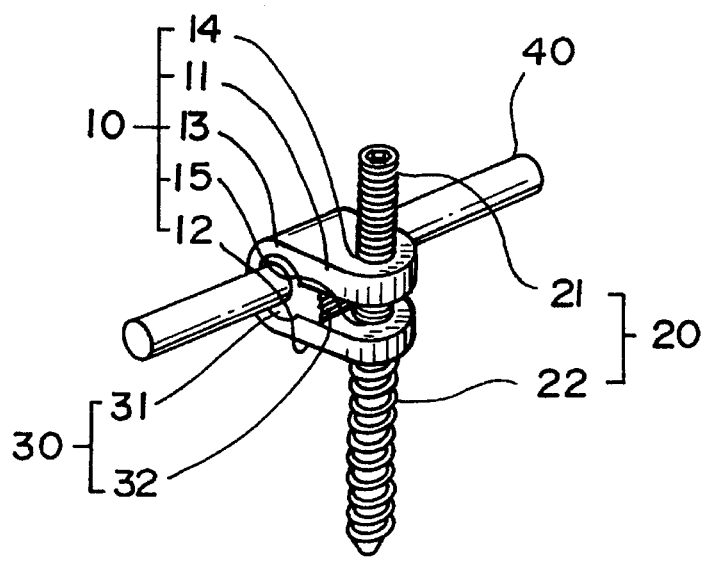
FIG. 1 shows a schematic view of an embodiment in combination according to the present invention.
Figure 2A:
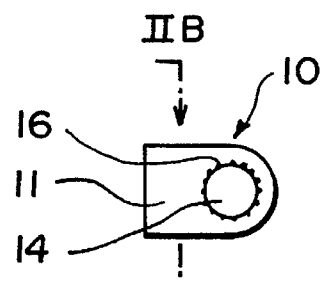
FIG. 2-A is a top plan view of a U-shaped clamping block incorporated in the holding and fixing mechanism of the present invention.
Figure 2B:
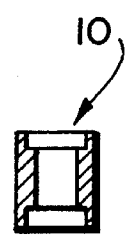
Figure 2C:
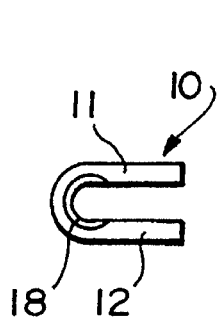
Figure 2D:
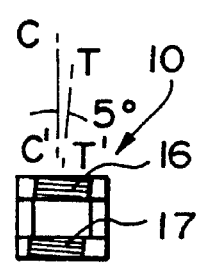
Figure 2E:
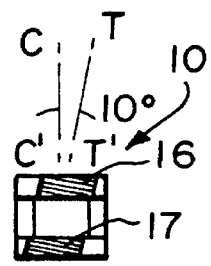
Figure 2F:
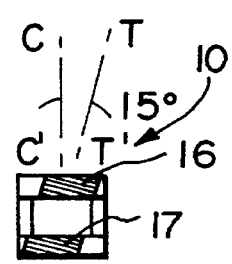

As shown in FIG. 1, the holding and fixing mechanism embodied in the present invention comprises a U-shaped clamping block 10, a wedging element 20, a holding plug 30, and a rod body 40. The U-shaped clamping block 10 is made up of a right plate 11, a left plate 12 and a curve portion 13. The right plate 11 and the left plate 12 are provided respectively with a through hole 14 and a through hole 15. The wedging element 20 consists of a wedging portion 21 provided thereon with knurls and of a fastening portion 22 (bone screw). The holding plug 30 is provided with a holding groove 31 and a knurled surface 32. The rod body 40 is in fact a vertebral fixation rod, which is held securely by the U-shaped clamping block 10, the wedging element 20, and the holding plug 30.

The various schematic views of the U-shaped clamping block 10 are shown in FIGS. 2-A to 2-F, in which the reference numerals 11–15 are similar in definition to the corresponding reference numerals of FIG. 1. FIG. 2-A shows a top plan view of the U-shaped clamping block 10 having a through hole 14 provided with knurls 16. FIG. 2-B is a side elevational view taken along the direction indicated by a line IIB—IIB as shown in FIG. 2-A. FIG. 2-C is a front elevational view of the U-shaped clamping block having a curve portion which is provided with a bevel groove 18 into which the holding plug is inserted. FIGS. 2–6 to 2-F are schematic views showing the knurl directions of the knurls 16 and 17 of the two through holes 14 and 15 of the U-shaped clamping block. The axial directions TT' of the knurls and the vertical axial direction CC' of the two plates of the U-shaped clamping block form various specific angles, which are respectively 5°, 10°, and 15°.

Figure 3A:
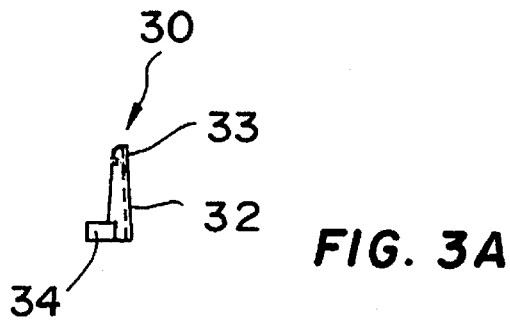
FIG. 3-A is a top plan view of a holding plug incorporated in the holding and fixing mechanism of the present invention.
Figures 3B, 3C, 3D, 3E:
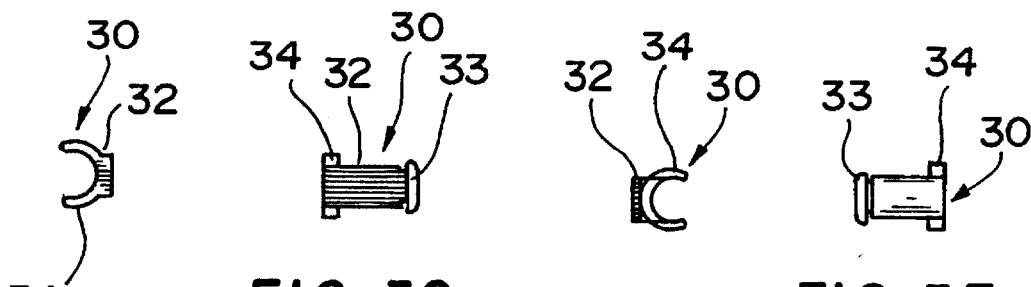

FIG. 3-A is a top plan view of the holding plug 30 which comprises a knurled surface 32, an elastic inverted retaining element 33 which here constitutes a hook member 34 defining a columnar holding hole and the holding groove 31. The knurled surface 3-B is oblique. FIGS. 3-2 to 3-E include respectively a front elevational view of the holding plug 30, a right elevational view of the holding plug 30, a rear elevational view of the holding plug 30, and a left elevational view of the holding plug 30. The reference numerals of 31, 32 and 33 of FIGS. 3-B to 3-E are similar in definition to the like reference numerals of FIG. 3-B. As the holding plug 30 is located after being pressed, the holding plug 30 can be retained on the U-shaped clamping block 10 of FIG. 1, thanks to the elastic inverted retaining element 33.

Figure 4:
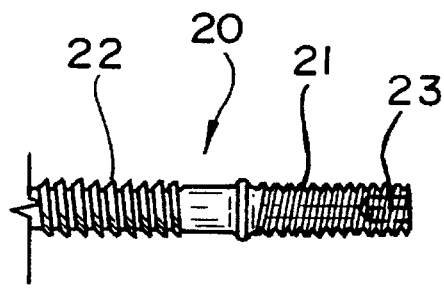
FIG. 4 shows a schematic view of the wedging element of the present invention.

As shown in FIG. 4, the wedging element 20 comprises a wedging portion 21, a fastening element 22, and a tool hole 23 located in the top end thereof.

Figures 5, 6:
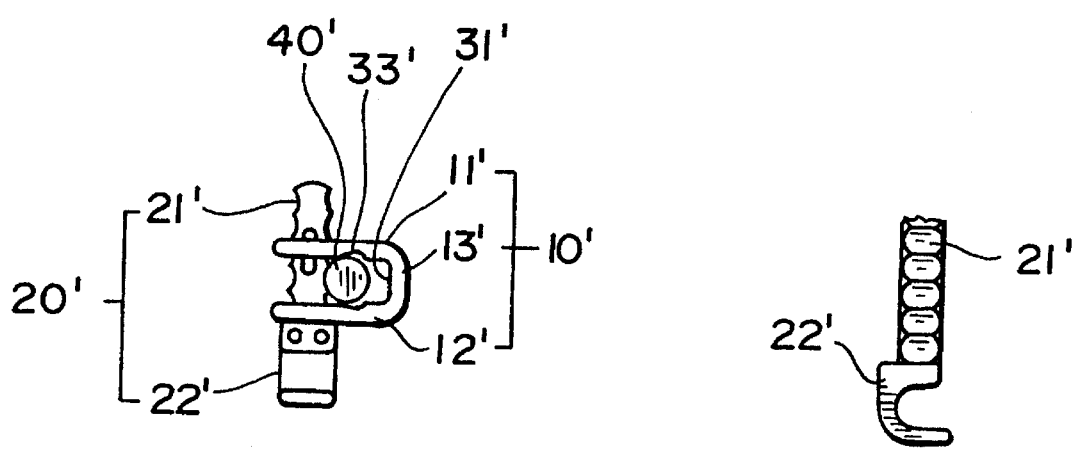
FIG. 5 shows a schematic view of another preferred embodiment in combination according to the present invention.
FIG. 6 is a side elevational view of the bone hook as shown in FIG. 5.

A second preferred embodiment of the present invention is schematically shown in FIG. 5 in which the reference numerals are similar in definition to the like reference numerals of FIGS. 1 and 3. The second preferred embodiment comprises a bone hook serving as the fastening element 22', and the wedging portion 21' having parallel grooves in place of the knurls of the first preferred embodiment as shown in FIG. 1. Furthermore, the second preferred embodiment comprises a holding plug provided with an oblique surface 31' devoid of knurls. The rod body 40' is held securely in a hollow cavity or columnar holding hole formed by the holding groove of the holding plug and the parallel grooves of the wedging portion of the wedging element.

The second preferred embodiment of the present invention is modified in such a manner that the wedging portion 21' of the wedging element 20 is provided with parallel grooves, and that a bone hook 22 is used to serve as the fastening element of the wedging element 20', as illustrated in FIG. 6.

Figure 7:
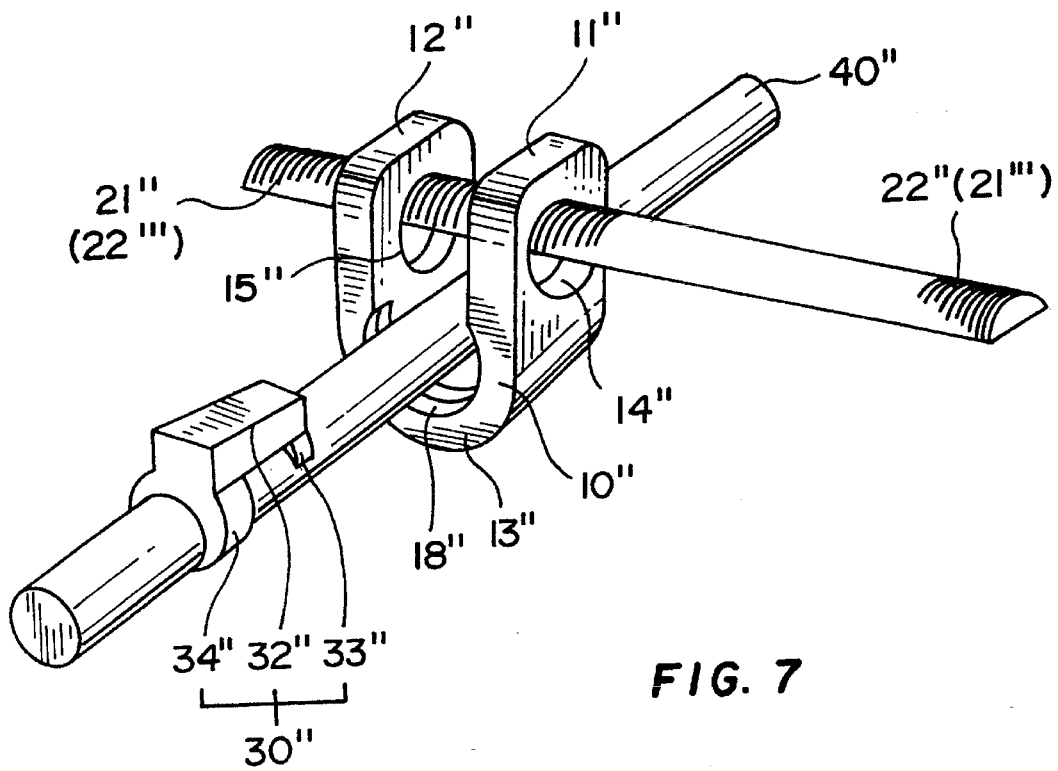
FIG. 7 shows a schematic view of still another preferred embodiment in combination according to the present invention.

A third preferred embodiment of the present invention is shown in FIG. 7 in which the reference numerals are similar in definition to the like reference numerals of FIGS. 1, 2 and 3. The third preferred embodiment is different from the first preferred embodiment in that the former comprises an auxiliary fixation rod in place of the wedging element. As a result, the wedging portion 21' is the fastening portion 22''' and the fastening portion 22" is the wedging portion 21' of another holding and fixing mechanism.

Figure 8:
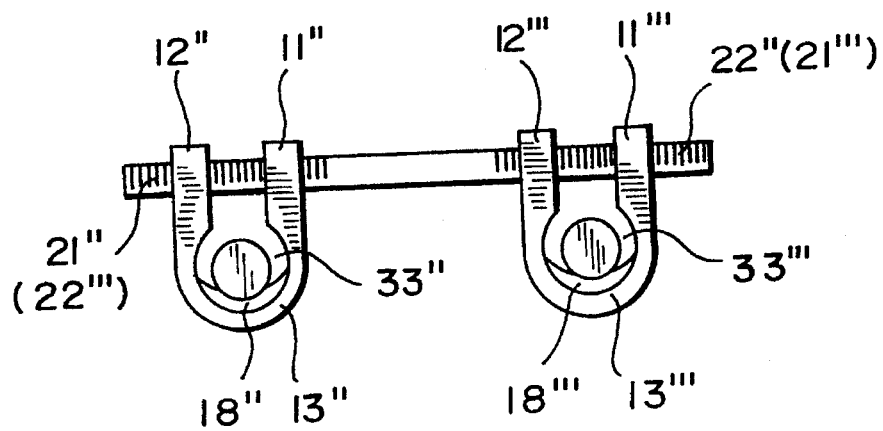
FIG. 8 is a schematic view showing that two sets of the preferred embodiment as shown in FIG. 7 are combined to work side by side.

Two sets of the third preferred embodiment as illustrated in FIG. 7 may be combined to work side by side, as shown in FIG. 8 in which the reference numerals of 11", 12", 13", 18", 21"(22'''), 22"(21''') and 33" are similar in definition to the like reference numerals of FIG. 7. In addition, the reference numerals of 11''',12''', 13''', 18''' and 33''' are similar in definition to the reference numerals of 11, 12, 13, 18 and 33 respectively.

The application of the holding and fixing mechanism of the present invention to the surgical treatment of a deformed or injured bone is described explicitly hereinafter.

The first preferred embodiment as shown in FIG. 1 is used as an example for illustrating the surgical application of the present invention. As soon as the bone screw 20 is fastened onto a vertebra intended to be fixed, the vertebral fixation rod 40 must be held by the curve portion 13 of the U-shaped clamping block 10 such that the wedging portion 21 of the bone screw 20 is held securely in the through holes 14 and 15 so as to fix the vertebral fixation rod 40. The wedging portion 21 and the knurl positions of the through holes 14 and 15 must be so adjusted as to permit the holding plug 30 to be inserted mechanically such that the holding groove 31 of the holding plug 30 and the curve portion 13 of the U-shaped clamping block 10 form a holding hole of a columnar construction, which holds securely the vertebral fixation rod 40. In the meantime, the knurled surface 32 of the holding plug 30 urges the wedging portion 21 of the bone screw 20 such that the knurls of the knurled surface 32 are fixed solidly in place with the knurls of the wedging portion 21 of the bone screw 20.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claim is:

1. A holding and fixing mechanism for an orthopedic surgery comprising:

a substantially curved U-shaped clamping block including a left plate and a right plate, which are each provided correspondingly and respectively with a through hole;

a wedging element having one end serving as a fastening element for fastening onto one of a vertebra and a vertebral fixation device, said wedging element further having another end serving as a wedging portion provided thereon with knurls, the wedging portion of said wedging element extending through the through hole provided in each of said left plate and said right plate of said U-shaped clamping block;

a rod body located between said U-shaped clamping block and said wedging element; and a holding plug lodged securely between said wedging portion of said wedging element and said rod body, said holding plug provided in one side thereof with a holding groove defining a columnar holding hole for holding therein securely said rod body, in conjunction with a curved portion of said U-shaped clamping block;

wherein a line extending through the through holes provided in said left plate and said right plate of said U-shaped clamping block forms a specific angle with an axis defined by the wedging portion of said wedging element, said specific angle ranging between 5° and 15°.

2. The holding and fixing mechanism of claim 1 wherein said holding grooves of said holding plug and said curved portion of said U-shaped clamping block form a hollow cavity in which said columnar holding hole is arranged and said rod body is held securely.

3. The holding a fixing mechanism of claim 2 wherein said wedging element comprises a vertebral auxiliary fixation rod.

4. The holding and fixing mechanism of claim 2 wherein said holding plug incorporates means for preventing said holding plug from being detached.

5. The holding and fixing mechanism of claim 4 wherein said wedging element comprises a bone screw.

6. The holding and fixing mechanism of claim 5 wherein said rod body constitutes a vertebral fixation rod.

7. The holding and fixing mechanism of claim 4 wherein said rod body constitutes a vertebral fixation rod.

8. The holding and fixing mechanism of claim 2 wherein said wedging element comprises a bone screw.

9. The holding and fixing mechanism of claim 8 wherein said rod body constitutes a vertebral fixation rod.

10. The holding an fixing mechanism of claim 2 wherein said rod body constitutes a vertebral fixation rod.

11. The holding and fixing mechanism of claim 1 wherein the curved portion of said U-shaped clamping block is provided with a bevel for receiving said holding plug; and wherein the knurls of said wedging portion is engageable with knurls provided on said holding plug.

12. A holding and fixing mechanism for an orthopedic surgery comprising:

a substantially curved U-shaped clamping block including a left plate and a right plate, which are provided correspondingly and respectively with a through hole;

a wedging element having one end serving as a fastening element for fastening onto one of vertebra and a vertebral fixation device, said wedging element further having another end serving as a wedging portion provided thereon with parallel grooves, the wedging portion of said wedging element extending through the through hole provided in each of said left plate and said right plate of said U-shaped clamping block;

a rod body located between said U-shaped clamping block and said wedging element; and a holding plug lodged securely between a curved portion of said U-shaped clamping block and said rod body, said holding plug provided in one side thereof with a holding groove defining a columnar holding hole for holding therein securely said rod body, in conjunction with said parallel grooves of said wedging portion of said wedging element;

wherein a line extending through the through holes provided in said left plate and said right plate of said U-shaped clamping block forms a specific angle with an axis defined by the wedging portion of said wedging element, said specific angle ranging between 5° and 15°.

13. The holding and fixing mechanism of claim 12 wherein said holding grooves of said holding plug and said knurls of said wedging portion of the wedging element form a hollow cavity for holding securely said rod body.

14. The holding and fixing mechanism of claim 13 wherein said holding plug incorporates a retaining means for preventing said holding plug from becoming detached.

15. The holding and fixing mechanism of claim 13 wherein said wedging element comprises a bone hook.

16. The holding and fixing mechanism of claim 15 wherein said rod body constitutes a vertebral fixation rod.

17. The holding and fixing mechanism of claim 13 wherein said rod body constitutes a vertebral fixation rod.

* * * * *